(12) United States Patent
Aghassian et al.

(10) Patent No.: US 8,933,944 B2
(45) Date of Patent: Jan. 13, 2015

(54) EXTERNAL CONTROLLER FOR AN IMPLANTABLE MEDICAL DEVICE WITH DUAL MICROCONTROLLERS FOR IMPROVED GRAPHICS RENDERING

(75) Inventors: Daniel Aghassian, Glendale, CA (US); Thomas Stouffer, Chatsworth, CA (US); Vuong Nguyen, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 579 days.

(21) Appl. No.: 13/218,049

(22) Filed: Aug. 25, 2011

(65) Prior Publication Data

US 2012/0092354 A1    Apr. 19, 2012

Related U.S. Application Data

(60) Provisional application No. 61/392,807, filed on Oct. 13, 2010.

(51) Int. Cl.
*G06F 15/80* (2006.01)
*A61N 1/372* (2006.01)
*G06F 19/00* (2011.01)

(52) U.S. Cl.
CPC ........ *A61N 1/37247* (2013.01); *G06F 19/3406* (2013.01)
USPC ........................................................ 345/505

(58) Field of Classification Search
CPC ..... G06T 1/20; G06T 15/005; G06T 2210/52; G09G 5/393; G09G 5/363
USPC .......................................................... 345/505
See application file for complete search history.

(56) References Cited

U.S. PATENT DOCUMENTS 5,123,419 A    6/1992  Platt et al.
5,496,349 A    3/1996  Campbell et al.
(Continued)

OTHER PUBLICATIONS

Precision Plus™ SCS System, http://www.chrisamichaels.com/assets/precplus.pdf, 2007.
(Continued)

*Primary Examiner* — Hau Nguyen
(74) *Attorney, Agent, or Firm* — Lewis & Reese, PLLC

(57) ABSTRACT

An improved external controller with dual microcontrollers useable with an implantable medical device is disclosed. The external controller comprises a low speed (low frequency) microcontroller and a high speed (high frequency) microcontroller. The low speed microcontroller receives telemetry data from the medical device, converts data into graphical commands, and transmits commands to the high speed microcontroller. The high speed microcontroller interprets the graphical commands, retrieves images indicative of the commands from a storage device, and renders the images onto a display screen. The high speed microcontroller may also process more complicated data sent from the low speed microcontroller, and return the results to the low speed microcontroller to allow it to form the graphics command for the high speed microcontroller to execute.

16 Claims, 7 Drawing Sheets

(56) References Cited

U.S. PATENT DOCUMENTS

| | | |
|---|---|---|
| 5,963,200 A | 10/1999 | Deering et al. |
| 5,974,341 A | 10/1999 | Er et al. |
| 6,516,227 B1 | 2/2003 | Meadows et al. |
| 6,594,523 B1 | 7/2003 | Levine |
| 7,432,921 B2 * | 10/2008 | Oshima et al. ............... 345/211 |
| 7,751,889 B1 | 7/2010 | Schecter |
| 7,853,330 B2 | 12/2010 | Bradley et al. |
| 8,098,251 B2 | 1/2012 | Chen |
| 2006/0224222 A1 | 10/2006 | Bradley et al. |
| 2009/0118796 A1 | 5/2009 | Chen et al. |
| 2011/0054559 A1 * | 3/2011 | Rosenberg et al. ............. 607/28 |

OTHER PUBLICATIONS

International Search Report and Written Opinion from the International Searching Authority, regarding corresponding application No. PCT/US2011/054874, dated Mar. 19, 2012.

* cited by examiner

EXTERNAL CONTROLLER FOR AN IMPLANTABLE MEDICAL DEVICE WITH DUAL MICROCONTROLLERS FOR IMPROVED GRAPHICS RENDERING

CROSS REFERENCE TO RELATED APPLICATIONS

This is a non-provisional application of U.S. Patent Application Ser. No. 61/392,807, filed Oct. 13, 2010, to which priority is claimed, and which is incorporated herein by reference in its entirety.

FIELD OF THE INVENTION

The present invention relates to an external controller for an implantable medical device having two microcontrollers and particularly useful in controlling a high resolution display on the external controller.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Pat. No. 6,516,227, which is incorporated herein by reference in its entirety.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 typically holds the circuitry and power source or battery necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

Portions of an IPG system are shown in FIG. 2 in cross section, and include the IPG 100 and an external controller (remote control) 210. The IPG 100 typically includes an electronic substrate assembly 14 including a printed circuit board (PCB) 16, along with various electronic components 20, such as microcontrollers, integrated circuits, and capacitors mounted to the PCB 16. Two coils are generally present in the IPG 100: a telemetry coil 13 used to transmit/receive data to/from the external controller 210; and a charging coil 18 for charging or recharging the IPG's power source or battery 26 using an external charger (not shown). The telemetry coil 13 can be mounted within the header connector 36 as shown, or can be included within the case 30.

As just noted, an external controller 210, such as a handheld programmer or a clinician's programmer, is used to wirelessly send data to and receive data from the IPG 100. For example, the external controller 210 can send programming data to the IPG 100 to set the therapy the IPG 100 will provide to the patient. Also, the external controller 210 can act as a receiver of data from the IPG 100, such as various data reporting on the IPG's status.

The communication of data to and from the external controller 210 occurs via magnetic inductive coupling. When data is to be sent from the external controller 210 to the IPG 100 for example, coil 17 is energized with an alternating current (AC). Such energizing of the coil 17 to transfer data can occur using a Frequency Shift Keying (FSK) protocol for example, such as disclosed in U.S. patent application Ser. No. 11/780,369, filed Jul. 19, 2007, which is incorporated herein by reference in its entirety. Energizing the coil 17 induces an electromagnetic field, which in turn induces a current in the IPG's telemetry coil 13, which current can then be demodulated to recover the original data. Communication from the IPG 100 to the external controller 210 occurs in essentially the same manner.

A front view of an external controller 210 is illustrated in FIG. 3. As shown, the external controller typically comprises a user interface, which includes various input buttons 250 and a display 440. The user interface may comprise other audible or tactile aspects as well. Using the user interface, the patient can perform various functions. For example, the user can adjust stimulation parameters using the buttons 250, which button presses can cause changes on a gauge on the display 440, such as the increase or decrease of stimulation power. Or, the display 440 can indicate status information with or without the pressing of buttons 250, such as the status of the battery 26 (FIG. 2) in the IPG 100. Further details concerning the structure and functionality of an external controller can be found in U.S. patent application Ser. No. 11/935,111, filed Nov. 5, 2007, with which the reader is assumed familiar.

As external controllers 210 and IPG 100 become more advanced, the inventors have noticed that it is advantageous to provide a richer user interface to the patient, such as a higher resolution, color display. For example, patients can currently use their external controllers 210 to steer current between electrodes to find a stimulation therapy that is most beneficial, such as Occurs using Boston Scientific's i-Sculpt™ technology. See http://www.chrisamichaels.com/assets/precplus- .pdf, a copy of which is filed with this application. But current steering is difficult using the microcontrollers and displays present in traditional external controllers, which typically use a monochrome liquid crystal display that is relatively simple to drive and does not require significant computing resources. Larger, higher resolution displays would better enable current steering and other system functionality, but this requires additional computing resources, which resources are difficult to provide using the microcontrollers present in previous external controllers. This disclosure provides a solution.

DETAILED DESCRIPTION

The description that follows relates to use of the invention within a spinal cord stimulation (SCS) system. However, the invention is not so limited. Rather, the invention may be used with any type of implantable medical device system that could benefit from an improved external controller for an implanted medical device. For example, the present invention may be used as part of a system employing an implantable sensor, an implantable drug pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

An improved external controller with dual microcontrollers useable with an implantable medical device is disclosed. The external controller comprises a low speed (low frequency) microcontroller and a high speed (high frequency) microcontroller. The low speed microcontroller receives telemetry data from the medical device via a telemetry unit, converts data into graphical commands, and transmits commands to the high speed microcontroller. The high speed microcontroller interprets the graphical commands, retrieves images indicative of the commands from a storage device, and renders the screen and images onto a display screen. The high speed microcontroller may also process more complicated data sent from the low speed microcontroller, and return the results to the low speed microcontroller to allow it to form the graphics command for the high speed microcontroller to execute. The result allows for the implementation of higher quality graphics in the external controller, and a richer patient experience with the external controller.

Figure 3:
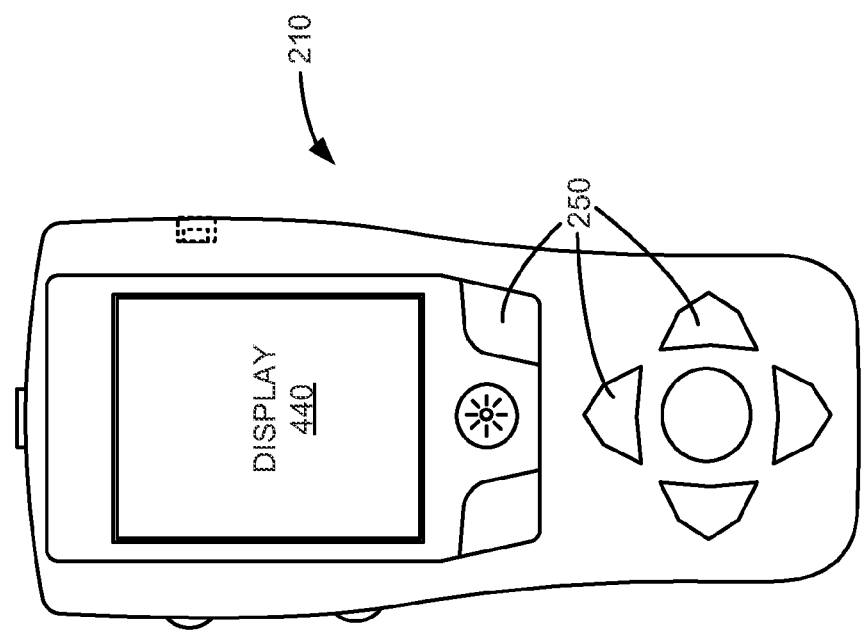
FIG. 3 shows an external controller of the prior art.
Figure 4:
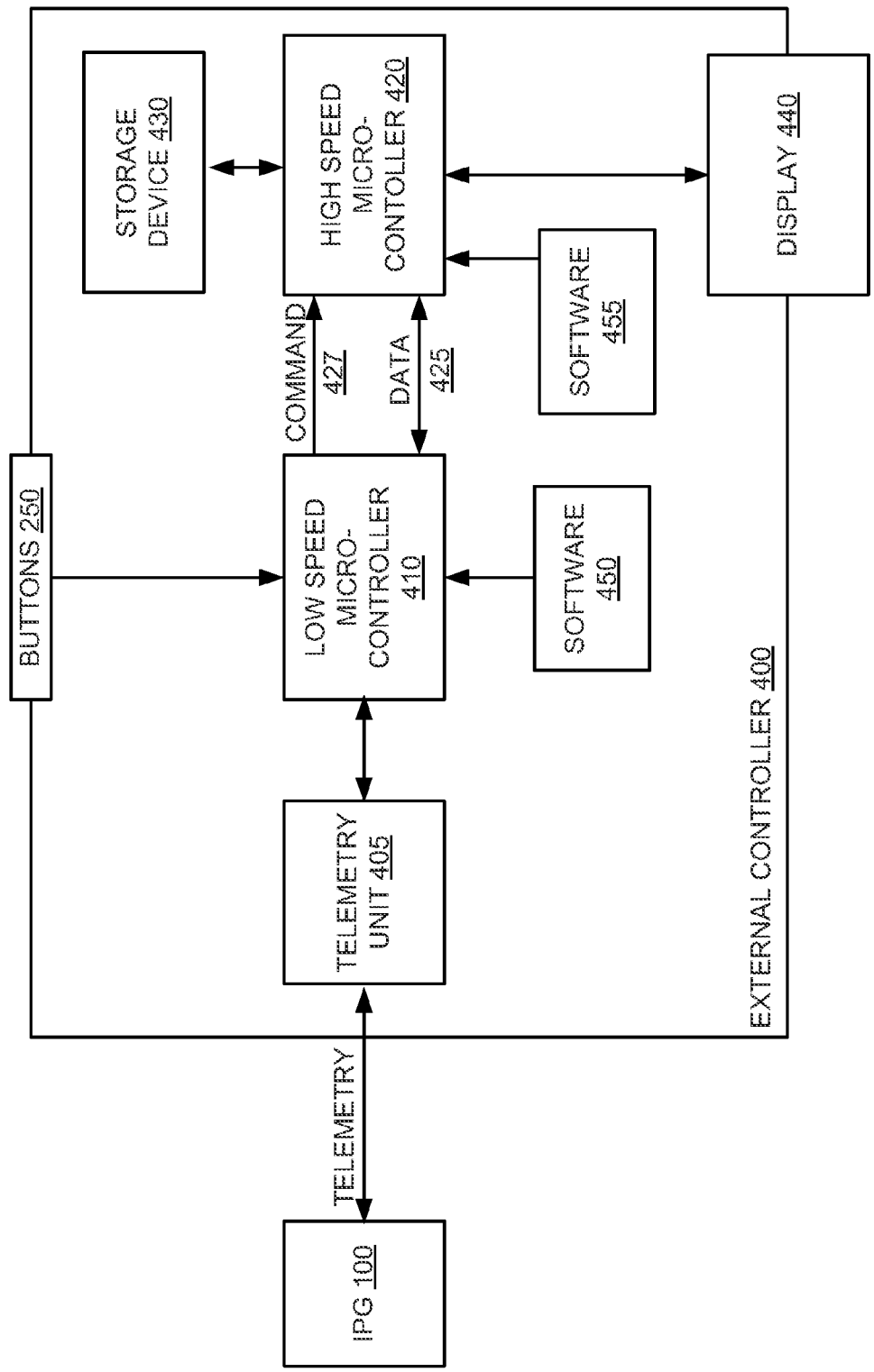
FIG. 4 shows in block diagram form an external controller with dual microcontrollers according to one embodiment.

One embodiment of the improved external controller 400 is illustrated in block diagram form in FIG. 4. The external controller 400 comprises two microcontrollers: a low speed microcontroller 410 and a high speed microcontroller 420, which will be discussed in detail below. The external controller 400 comprises a telemetry unit 405 which wirelessly communicates with the IPG 100. The external controller 400 also comprises a storage device 430 to store preloaded data, such as image files as discussed further below. The external controller 400 also provides a user interface to the patient in the form of a display 440 and various input buttons 250 (FIG. 3). From this user interface, the patient can perform a number of tasks, such as telemetering data (such as a new therapy program) from the external controller 400 to the IPG 100, monitoring at the external controller 400 various forms of status feedback from the IPG 100, etc. Typically such user input (e.g., from buttons 250) arrives at the low speed microcontroller 410, which acts as the master of the two microcontrollers 410 and 420, as explained further below.

In one embodiment, the external controller 400 always acts as the initiator of telemetry with the IPG 100. In this embodiment, the user uses the user interface to wake up the external controller 400 from a power down or "sleep" condition, and uses the user interface (e.g., buttons 250) to initiate such communications, such as querying the status of the IPG's battery. However, this is not strictly necessary in al useful embodiments. Instead, the external controller 400 can initiate communications with the IPG 100 without user intervention, or the IPG 100 can telemeter data (or at least attempt to telemeter data) to the external controller 400 on its own according to a schedule or when it receives data considered important.

The display 440 optimally displays both text and graphics to convey necessary information to the patient such as menu options; stimulation settings; IPG battery status; external controller battery status; stimulation status (i.e., on or off); charging status (on or off), etc. The display 440 may comprise a color display such as a color super twisted nematic (CSTN) or thin-film transistor (TFT) LCDs. The display 440 may further comprise an organic light-emitting diode (OLED) display. OLED displays are available in monochrome, grayscale (typically 4-bit), color (usually two or three colors), or full-color (8-bit to 32-bit color). As noted earlier, the complexity of the display 440 provides the primary motivation for the use of the dual microcontrollers 410 and 420.

Storage device 430 is used to store persistent data, such as image files which can be rendered on the display 440, as will be discussed further below. Such image files may be loaded into the storage device 430 during manufacturing of the external controller 400. The software block 450 generally contains the operating software for the low speed microcontroller 410, while software block 455 generally contains the operating software for the high speed microcontroller 420. Either of software blocks 450 or 455 may comprise a portion of the firmware of their respective microcontrollers, or may be connected thereto. Typically, both the storage device 430 and the software blocks 450 and 455 could comprise flash EEPROM memory, which provides for non-volatile storage, but which can be erased should updates to the operating software or the image files be required during or after manufacture. Alternatively, storage device 430 and software blocks 450 and 455 can be implemented in ROM microcode. Storage device 430 may be serially connected to the high speed microcontroller 420.

The low speed microcontroller 410 is suited for basic data processing in the external controller 400. The low speed microcontroller 410 has low power consumption due to its relatively low operating frequency (e.g., 6 MHz), has low electromagnetic emissions, and is relatively small in size. In one embodiment, a Texas Instruments MSP430 series microcontroller is used as a low speed microcontroller 410. The low speed microcontroller 410 handles telemetry and typical data processing in the external controller 400, which (compared to a modern-day personal computer for example) can occur relatively slowly.

The high speed microcontroller 420, by contrast, operates at higher frequencies (e.g., 48 MHz), and is therefore better adapted for performing functions requiring significant processing, such as heavy-computation, floating-point operations, or faster data streaming. In one embodiment, an Atmel ARM microcontroller is used as the high speed microcontroller 420.

As shown in FIG. 4, the external controller 400 can send and receive telemetry data to and from the IPG 100 at the low speed microcontroller 410 via the telemetry unit 405. Telemetry unit 405 includes transceiver circuitry, including modulation circuitry for encoding data for transmission and demodulation circuitry for decoding received data. As noted earlier, the external controller 400 can send programming data to the IPG 100 to set the therapy the IPG 100 will provide to the patient. The external controller 400 can also act as a receiver of data from the IPG 100, such as various data reporting on the IPG's status, which can be displayed on the display screen 440 for example.

As shown in FIG. 4, the low speed microcontroller 410 communicates with the high speed microcontroller 420 via a data bus 425. A separate control bus 427 for sending commands from the low speed 410 to the high speed 420 microcontroller is also shown. In this regard, the low speed microcontroller 410 acts as the "master" to the high speed microcontroller 420, which acts as the "slave" because it generally operates pursuant to the commands it is given by the low speed microcontroller 410. The data bus 425, the command bus 427, or both can comprise a serial bus.

As noted above, the external controller 400 receives telemetry data from the IPG 100 at the low speed microcontroller 410 via the telemetry unit 405, such as the capacity of the IPG 100's battery, which information is to be sent to the display 440. To facilitate this operation, the low speed microcontroller 410 converts the received telemetry data into graphics commands to be executed by the high speed microcontroller 420. A graphic command comprises a set of instructions of how to draw or update a screen, and such graphics commands can be formatted in accordance with a graphic command protocol. Of course, not all data transmitted from the IPG 100 to the external controller 400 will comprise data ultimately destined for the display 440, and in such instances graphical command formatting is unnecessary. Moreover, not all imagery on the display 440 will result from data telemetered from the IPG 100, although displaying telemetered data will be emphasized in the example that follows.

The graphic command protocol used in the external controller 400 uses a library of indexed screens, which each screen or index corresponding to a particular look of the screen at any given time during operation of the external controller 400. For example, index 0 may comprise the "main menu" screen, which may present the user a variety of selections, while index 1 may comprise the "stimulation screen." The user may move between these screens by making a selection using the user interface: for example, using buttons 250, he may move from the main menu screen (index 0) to the stimulation screen (index 1). However, this is not strictly required, as the external controller 400 can also automatically move between screens (indices) as necessary to show the user various information of importance.

Figure 5B:
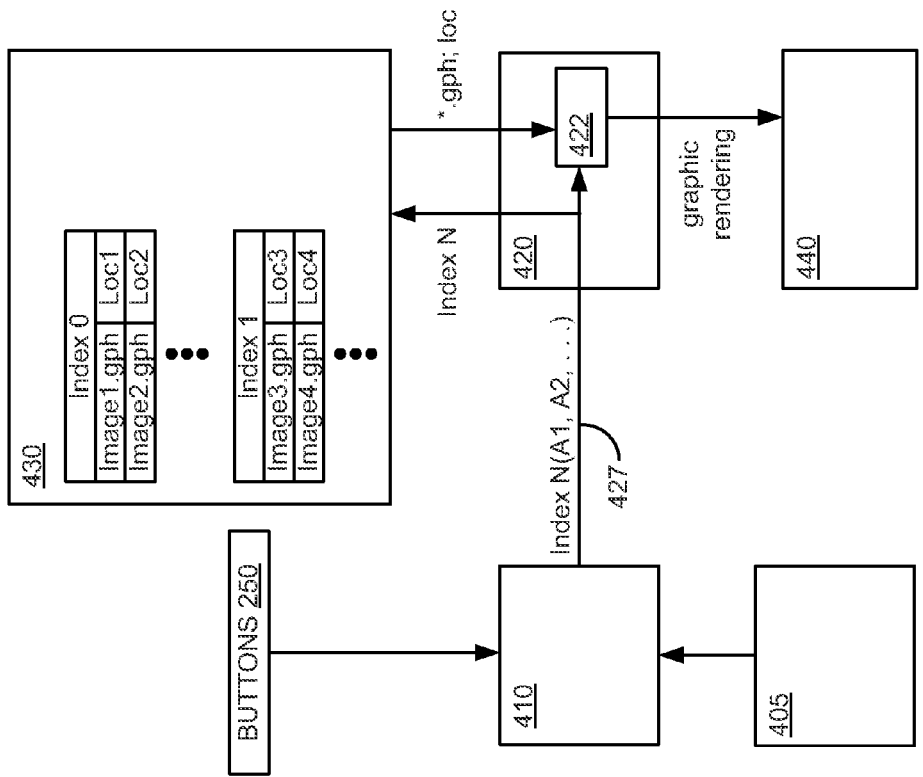
FIGS. 5A and 5B show an example display screen, and an example flow to render graphics on the display screen in an external controller with dual microcontrollers according to one embodiment.
Figure 5A:
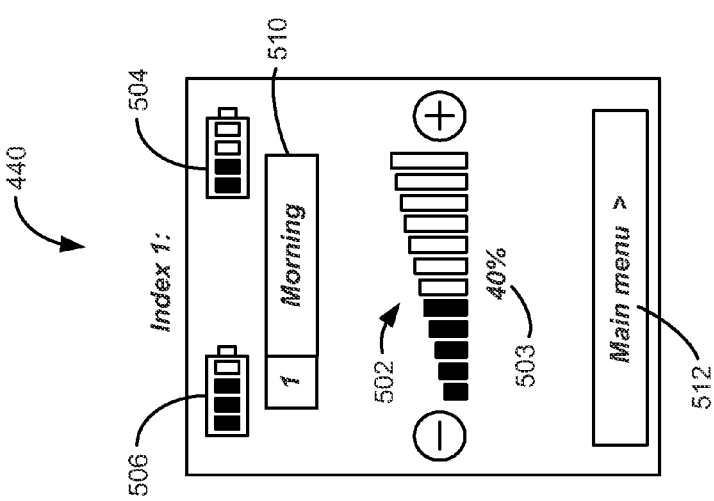

Each index defines a layout for the display 440, and corresponds to set of graphics to be displayed on the display 440 and their locations. An example "stimulation screen" display with index 1 is shown in FIG. 5A, which includes graphics for the status of the external controller's battery 506, the IPG's battery 504, the level of simulation 502, the level of stimulation written in text as a percentage of maximum 503, a program graphic 510, and a menu graphic 512. The program graphic 510 contains a particular program number ('1' as shown) as well as a textual description of that program ("morning"), which denotes that this program '1' contains settings typically used by the patient in the morning. Of course, the program number, and its settings, can be changed by the user using the user interface.

Some of these graphics displayed for a particular screen index can include attributes that will vary the graphic displayed. For example, the IPG battery gauge 504 is based on the current capacity of the IPG battery, which can range from 0 to 100%. This capacity attribute is reflected in the gauge 504 as a number of solid bars (four bars each comprising 25% of capacity) as is typical. The level of stimulation gauge 502 is similar and constitutes a number of bars to indicate the current stimulation level as a percentage of maximum. Additionally, gauge 503 displays this attribute textually (e.g., 40%). Some of these attributes will result from changes made by the user, while other will result from data telemetered from the IPG 100. For example, IPG battery capacity as reflected by gauge 504 will result from data telemetered from the IPG 100, while stimulation level as reflected by gauges 502 and 503 will result from user input via buttons 250 on the external controller's user interface.

The low speed microcontroller 410 will know based on the data it is receiving (either from the IPG 100 via telemetry, or the user via the user interface) what screen index, or particular graphic in that screen index, is implicated. For example, telemetry data will be accompanied by header information identifying the telemetered data. The low speed microcontroller 410 will then pass that index and any attributes (Ax) (e.g., IPG battery capacity) to the high speed microcontroller 420 via the control bus 427, as shown in FIG. 5B. As noted earlier, each screen index corresponds to a plurality of image files corresponding to the graphics that constitute a given index, and these image files and locations are stored in the storage device 430 as shown. For example, image file "Image3.gph" may comprise the image file for the IPG battery gauge 504, and "Loc3" its location on the display 440, while "Image4.gph" may comprise the image file for the stimulation gauge 502, and Loc4 its location on the display.

When a new index is passed from the high speed microcontroller 420 to the storage device 430, the corresponding image files and locations are retrieved, again as shown in FIG. 5B. The high speed microcontroller 420 can then process these and render the appropriate graphics on the display 440 using its rendering engine 422. To the extent the graphic is modified by an attribute, such as the IPG battery capacity, the rendering engine 422 will consider the attribute, and modify the rendered image accordingly. For example, if the IPG battery capacity is very low (say 25%), the rendering engine will consider that attribute and cause only one of the four bars in the gauge 504 to be rendered solid. Additionally, the rendering engine 422 may also change the other aspects of the rendered image to change depending on attribute. For example, the gauge 504 may be rendered in a different color (red), or may be made to flash, if the IPG battery capacity is critically low. The rendering engine 422 may also update the displayed image as attributes change over time. For example, should the rendering engine 422 see that the IPG battery capacity is decreasing, it will adjust the rendered graphic for the gauge 504 accordingly.

Because of the high speed microcontroller 420's processing speed, the graphics can be rendered on the display seemingly instantaneously from the user's perspective. By contrast, were the low speed microcontroller 410 to perform such rendering on its own, its slow speed would make for a frustrating user experience, as the user would have to wait an undue length of time while the image was slowly rastered across the screen. Moreover, if the low speed microcontroller 410 were to perform the graphics rendering, it may become "bogged down" handling the required data to the point of neglect of other systems functions (e.g., telemetry). Fast graphics processing as enabled by external controller 400 allows current steering (such as iSculpt™ current steering technology as mentioned earlier) to be smoothly implemented. For example, the position of the electrodes will be shown on the display 440, and the user can then use buttons 250 to move or "steer" current between the electrodes to optimize his or her stimulation therapy.

Figure 6:
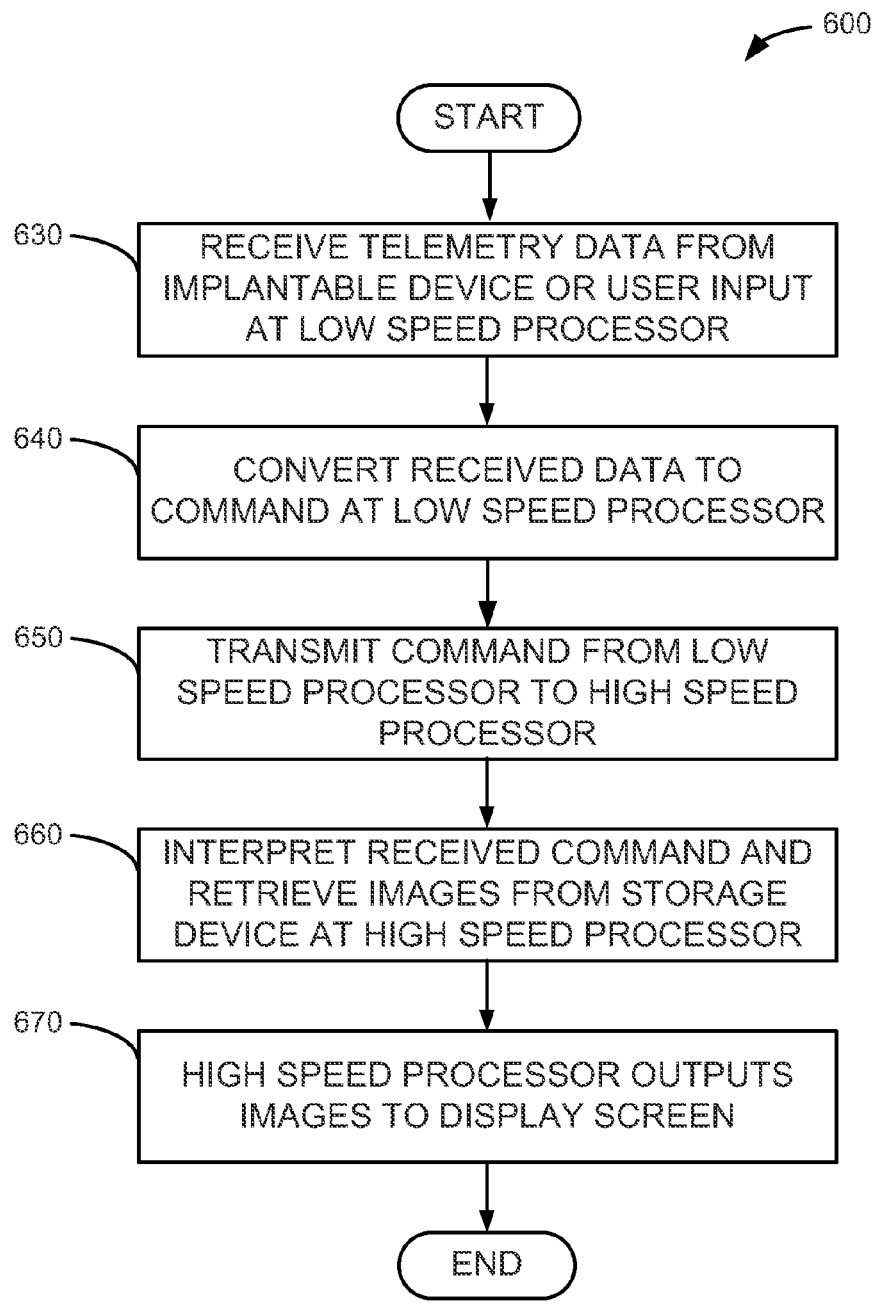
FIG. 6 shows in flow chart form a technique for processing telemetry data in an external controller with dual microcontrollers according to one embodiment.

FIG. 6 summarizes the technique as discussed so far in flow chart form. The external controller 400 receives telemetry data from the implantable device, or user input from the user interface, at the low speed microcontroller 410 (step 630). The low speed microcontroller 410 then converts the received data into commands in accordance with a command protocol (step 640). The commands are then transmitted from the low speed microcontroller 410 to the high speed microcontroller 420 via the control bus 427 (step 650). Once the high speed microcontroller 420 receives the commands, it interprets the commands, and retrieves the corresponding image files from the storage device 430 (step 660). The high speed microcontroller 420 then renders the images on the display screen 440 (block 670).

Figures 1A, 1B:
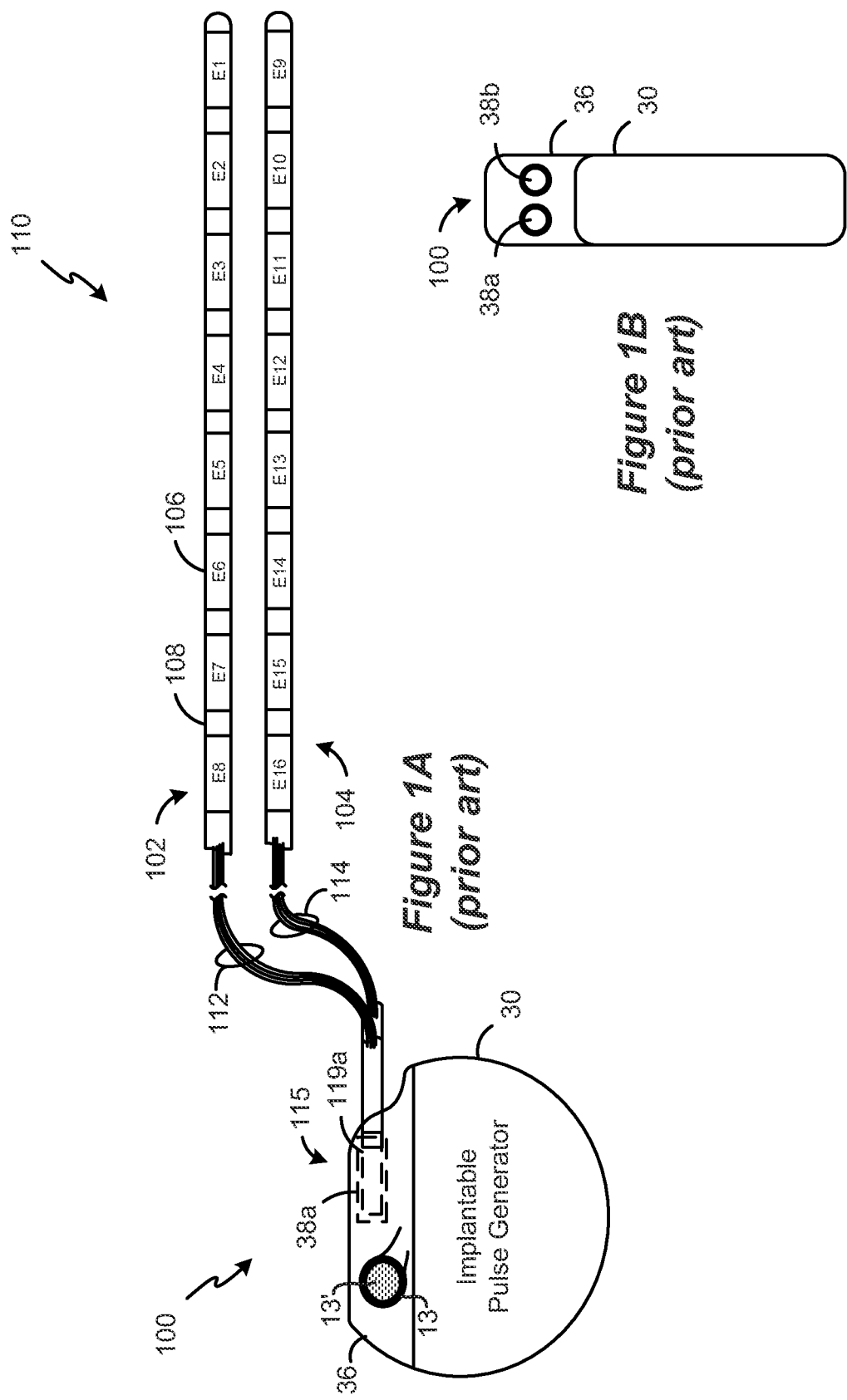
FIGS. 1A and 1B show an implantable pulse generator (IPG), and the manner in which an electrode array is coupled to the IPG in accordance with the prior art.
Figure 2:
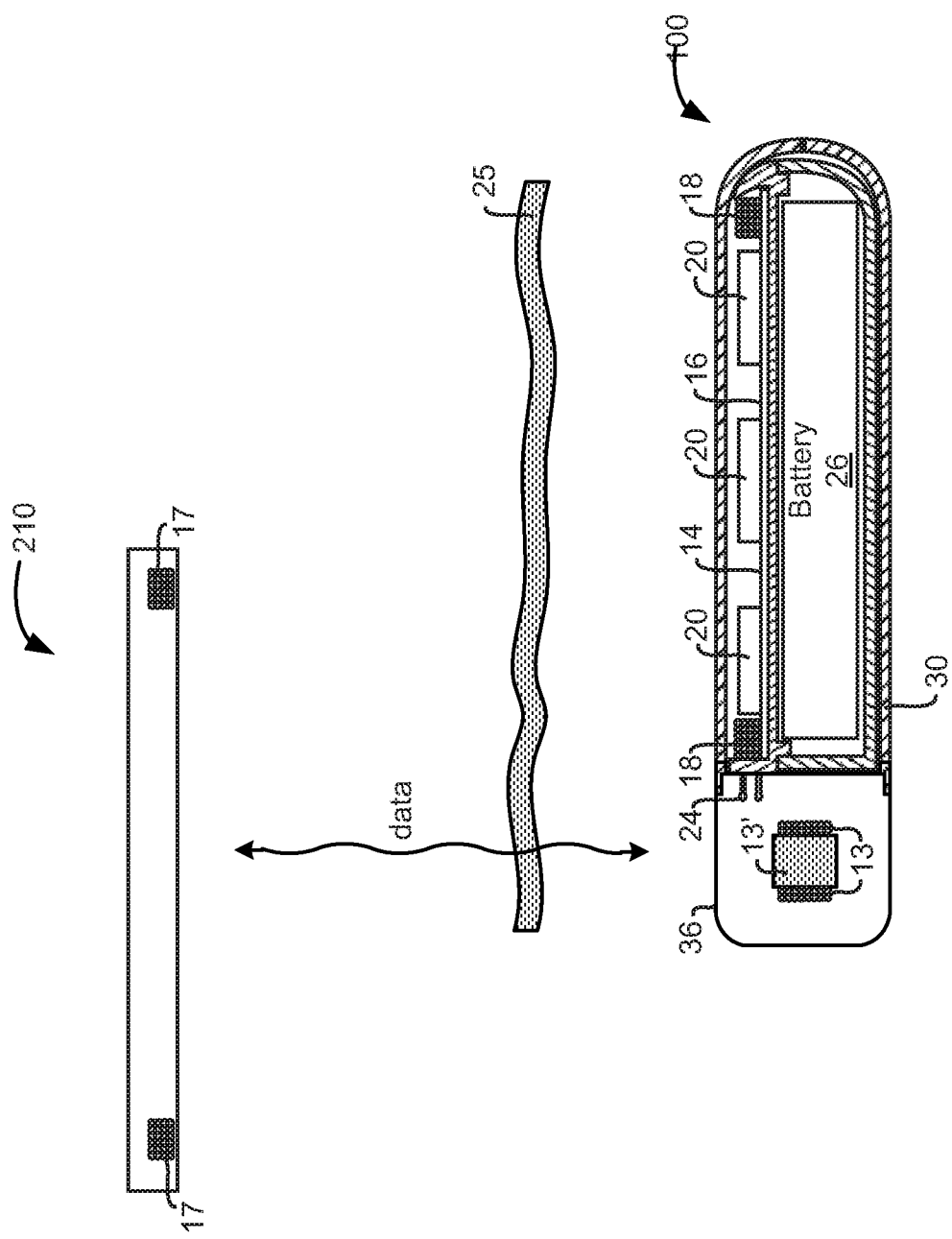
FIG. 2 shows wireless communication of data between an external controller and an IPG.

Certain data sent from the IPG 100 may require significant processing at the external controller 400 before it can be rendered on the display 440. For example, certain information received from the IPG 100 can be complicated, such as information regarding the relative positioning of the electrodes as implanted in the patient. Such positioning information can be used to draw an image on the display 440 of the electrode leads 102 and 104 (FIG. 1A), which can allow the patient to understand whether such leads have moved into improper positions. Such positing information usually includes various resistance measurements taken between the various different electrodes in the leads, and because of the multivariable nature of the data, significant processing is required to interpret such resistance values into positions renderable on the display 440. The techniques of calculating electrode positions are disclosed in U.S. patent application Ser. No. 11/096,483, filed Apr. 1, 2005 and Ser. No. 11/938,490, filed Nov. 12, 2007, with which the reader is assumed familiar. As one might expect, the IPG 100 is not well suited for processing such resistance values, because processing capability in the IPG 100 is limited. Instead, the resistance values are telemetered from the IPG 100 to the external controller 400 for processing. The low speed microcontroller 410 is also not well suited for processing such data, because the speed and processing power of such microcontroller is limited.

Therefore, in another embodiment of the technique, data received at the low speed microcontroller 410 is assessed to determine whether it requires further processing prior to command generation and rendering on the display 440. If so, i.e., if the telemetered data is relatively complicated and requires significant processing prior to rendering onto the display 440, such as with the resistance values discussed above, such data is sent by the low speed microcontroller 410 to the high speed microcontroller 420 for such processing, which processed data is then sent back to the low speed microcontroller 410 to be converted into graphical commands. By contrast, if the received data is relatively simple and is ready to be displayed to the patient with only minimal processing, such as IPG battery status, the low speed microcontroller 410 processes the data pursuant to the flow of FIG. 6 discussed above.

Figure 7:
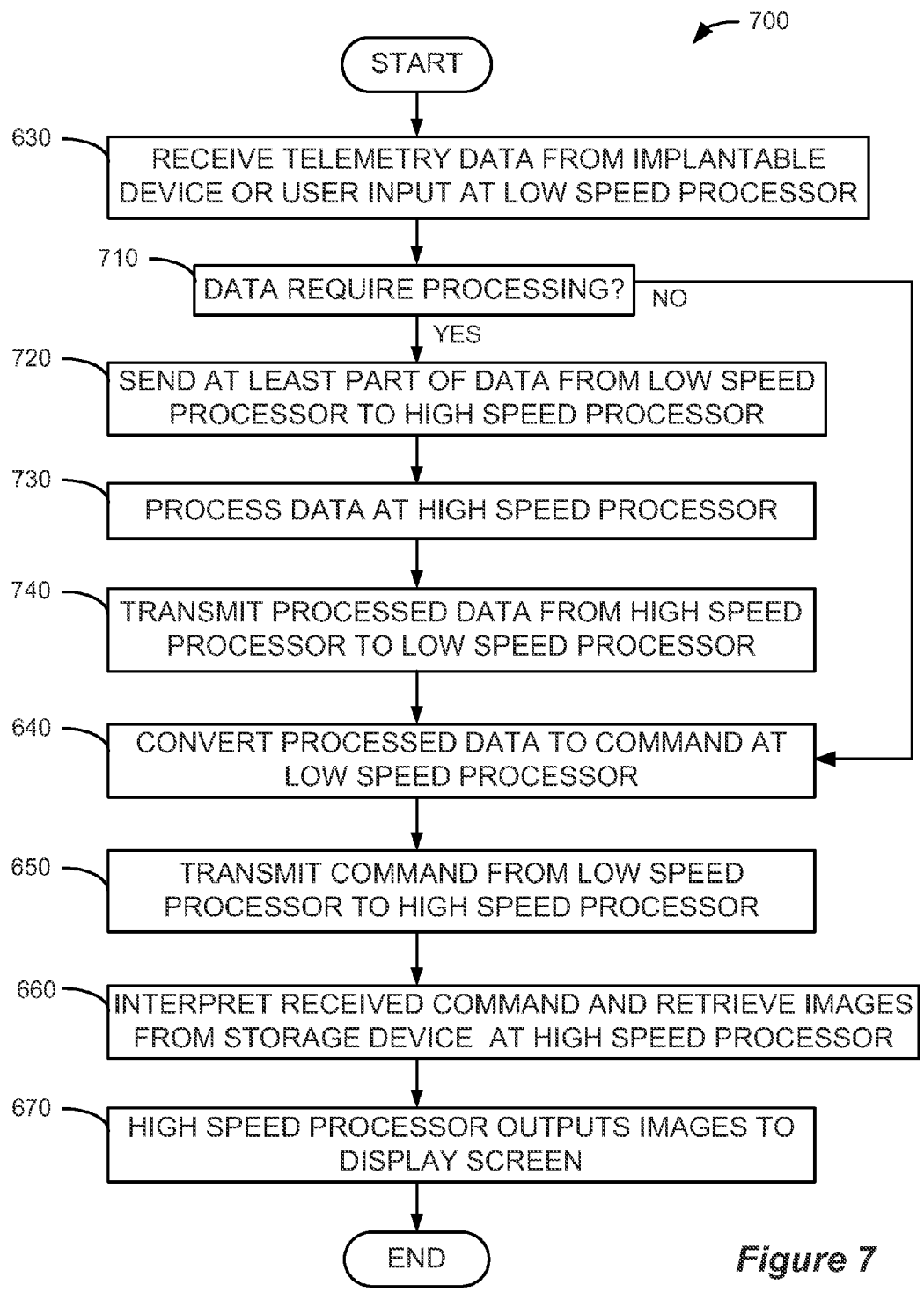
FIG. 7 shows in flow chart form a technique for processing telemetry data in an external controller with dual microcontrollers according to another embodiment.

The process 700 for this embodiment is illustrated in FIG. 7. As before, telemetered data or user input is assessed by the low speed microcontroller 410 at step 710 to determine whether further data processing is required prior to graphics rendering. Because the low speed microcontroller 410 knows the various types of data it receives from the IPG 100, such assessment can merely involve identifying the type of data received. If further data processing is not needed, the process continues to steps already discussed with respect to FIG. 6. That is, the data is converted to a graphical command (640); transmitted to the high speed microcontroller 420 (650); used to retrieve images at the high speed microcontroller 420 (660); and rendered on the display 440 by the high speed microcontroller 420 (670).

However, if the data requires further processing at step 710, the low speed microcontroller 410 then transmits at least a portion of the data to the high speed microcontroller 420 along the data bus 425 (step 720). Those portions of the data transmitted to the high speed microcontroller 420 will logically comprise those requiring significant processing, such as mathematical analysis, as would be the case for the resistance values discussed earlier. By contrast, other portions of received data not requiring processing can simply be held in memory at the low speed microcontroller 410 pending completion of processing of the remainder at the high speed microcontroller 420.

The data transmitted to the high speed microcontroller 420 is then processed (step 730), and transmitted back to the low speed microcontroller 410 via the data bus (step 740). At this point, it can be combined with any received data held at the low speed microcontroller 410 and converted to a graphics command (640); transmitted to the high speed microcontroller 420 (650); used to retrieve images at the high speed microcontroller 420 (660); and rendered on the display 440 (670), as described above with respect to FIG. 6. In the resistance value example discussed earlier, location data would comprise attributes accompanying the graphics command at step 640.

The improved external controller 400 with dual microcontrollers provides several advantages. With the addition of the high speed microcontroller 420 and the improved high-resolution color display 440, the external controller 400 can provide richer user options and feedback to a patient. Moreover, the dual microcontrollers also provide parallel processing capability, allowing the high speed microcontroller 420 to update graphics on the display 440 while permitting the low speed microcontroller 410 to perform other tasks, such as telemetry and other system functions. Additionally, the low speed microcontroller 410 is preferred for running the telemetry functions, as it lower operating frequency is at less risk to interfere with telemetry.

It should be understood that the "microcontrollers" referred to in this disclosure can comprise microprocessors or other logic devices (e.g., FPGAs) as well, and are preferably implemented as discrete integrated circuits.

It should be understood that a graphics command used to render an image on the display may in an actual implementation comprises a plurality of graphics commands. Therefore, a graphics command should be interpreted either as a single command, or as a string of graphics commands.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for rendering at least one graphic on a display of an external medical device, comprising:

receiving at a first microcontroller input data telemetered from an implantable medical device, wherein the input data comprises at least one attribute, and wherein each attribute is associated with a graphic to be rendered on the display;

converting the input data to a graphics command at the first microcontroller, the graphics command comprising a screen index and the at least one attribute, wherein the screen index corresponds to a set of graphics to be rendered on the display and the location of the graphics on the display;

transmitting the graphics command to a second microcontroller;

receiving at the second microcontroller at least one image file and a location associated with each image file from a storage device using the screen index, wherein each image file corresponds to a graphic to be rendered;

modifying at the second microcontroller each graphic in accordance with its associated attribute; and using the second microcontroller to render each modified graphic using its corresponding image file, wherein each modified graphic is rendered at the location on the display associated with the image file corresponding to the graphic.

2. The method of claim 1, wherein the first microcontroller operates at a slower clock frequency than does the second microcontroller.

3. The method of claim 1, wherein the input data can additionally be received from a user interface of the external controller.

4. The method of claim 3, wherein the user interface comprises a plurality of buttons.

5. The method of claim 1, wherein the input data comprises a capacity of a battery in the implantable medical device.

6. A method for rendering graphics on a display of an external medical device, comprising:
   (a) receiving at a first microcontroller input data telemetered from an implantable medical device, the input data indicative of at least one graphic to be rendered on the display;
   (b) transmitting at least a first part of the input data from the first microcontroller to a second microcontroller;
   (c) processing the at least first part of the input data at the second microcontroller;
   (d) transmitting the processed data to the first microcontroller;
   (e) converting at least the processed data to a graphics command at the first microcontroller;
   (f) transmitting the graphics command to the second microcontroller;
   (g) retrieving at least one image file from a storage device using the graphics command; and
   (h) using the second microcontroller to render the at least one image file on the display.

7. The method of claim 6, further comprising storing a second part of the input data at the first microcontroller, and converting the processed data and the second part of the input data to the graphical command at the first microcontroller.

8. The method of claim 6, wherein steps (b) and (d) occur using a data bus between the first and second microcontrollers, and wherein step (f) occurs using a control bus between the first and second microcontrollers.

9. The method of claim 6, wherein the first microcontroller operates at a slower clock frequency than does the second microcontroller.

10. The method of claim 6, wherein the graphics command comprises a screen index.

11. The method of claim 10, wherein the graphics command further comprises at least one attribute, wherein the at least one attribute modifies the rendering of the graphic.

12. The method of claim 10, wherein the screen index is used to retrieve the at least one image file from the storage device.

13. The method of claim 6, wherein the graphics command is additionally used to retrieve a location for the at least one image file, and wherein the at least one graphic is rendered at the location on the display.

14. The method of claim 6, wherein the input data can additionally be received from a user interface of the external controller.

15. The method of claim 14, wherein the user interface comprises a plurality of buttons.

16. The method of claim 6, wherein the input data comprises electrode resistance values.

* * * * *